United States Patent
Yang et al.

(10) Patent No.: US 7,141,703 B2
(45) Date of Patent: Nov. 28, 2006

(54) PROCESS FOR PRODUCING PHENOL AND KETONE USING NEUTRALIZING BASE

(75) Inventors: Jiemin Yang, Houston, TX (US); Jesse Raymond Black, Katy, TX (US)

(73) Assignee: Shell Oil Company, Houston, TX (US)

( * ) Notice: Subject to any disclaimer, the term of this patent is extended or adjusted under 35 U.S.C. 154(b) by 44 days.

(21) Appl. No.: 10/761,641

(22) Filed: Jan. 21, 2004

(65) Prior Publication Data

US 2004/0162448 A1    Aug. 19, 2004

Related U.S. Application Data

(60) Provisional application No. 60/447,526, filed on Feb. 14, 2003.

(51) Int. Cl.
*C07C 409/00*    (2006.01)

(52) U.S. Cl. .................................... 568/577

(58) Field of Classification Search ............ 568/577
See application file for complete search history.

(56) References Cited

U.S. PATENT DOCUMENTS

| | | | |
|---|---|---|---|
| 2,632,026 A | 3/1953 | Conner, Jr. ............ | 260/610 |
| 2,632,773 A | 3/1953 | Armstrong et al. ...... | 260/610 |
| 2,757,209 A | 7/1956 | Joris ........................ | 260/621 |
| 3,187,055 A * | 6/1965 | Armstrong et al. ...... | 568/569 |
| 3,523,977 A * | 8/1970 | Reni et al. ................ | 568/574 |
| 3,907,901 A * | 9/1975 | Feder et al. .............. | 568/569 |
| 4,016,213 A * | 4/1977 | Yeh et al. ................. | 568/754 |
| 4,358,618 A | 11/1982 | Sifniades et al. ........ | 568/385 |
| 4,431,849 A * | 2/1984 | Colvin ..................... | 568/799 |
| 5,254,751 A | 10/1993 | Zakoshansky ........... | 568/798 |
| 5,767,322 A * | 6/1998 | Zakoshansky et al. ... | 568/571 |
| 5,908,962 A * | 6/1999 | Zakoshansky et al. ... | 568/571 |
| 5,959,155 A * | 9/1999 | Ohmae et al. ............ | 568/576 |
| 6,077,977 A | 6/2000 | Gopinathan et al. ..... | 568/571 |
| 6,465,695 B1 * | 10/2002 | Fulmer et al. ........... | 568/571 |

FOREIGN PATENT DOCUMENTS

| | | |
|---|---|---|
| DE | 1443329 | 1/1970 |
| DE | 2300903 | 1/1972 |
| EP | 0399776 | 5/1990 |
| JP | 03287574 | 12/1991 |
| WO | 00/14042 | 3/2000 |

* cited by examiner

*Primary Examiner*—Thurman Page
*Assistant Examiner*—Chukwuma Nwaonicha

(57) ABSTRACT

Improved processes for oxidizing alkylbenzene(s) to produce phenol and ketone product(s) using neutralizing base.

36 Claims, No Drawings

PROCESS FOR PRODUCING PHENOL AND KETONE USING NEUTRALIZING BASE

CROSS-REFERENCE TO RELATED APPLICATIONS

The present application claims the benefit of U.S. Provisional Patent Application Ser. No. 60/447,526, filed Feb. 14, 2003, pending.

FIELD OF THE APPLICATION

The present application relates to a process for producing phenol and ketone(s), preferably for producing phenol and acetone and/or methyl ethyl ketone (MEK).

BACKGROUND

Phenol is an important chemical parent substance with a broad usage spectrum. For example, phenol is used to produce phenol resins, bisphenol A, caprolactam, adipic acid, alkyl phenols, and plasticizers.

In general, phenol is manufactured by oxidizing alkylbenzene(s) to form hydroperoxide(s) followed by cleavage of the hydroperoxide(s) with an inorganic acid to form a hydroperoxide cleavage product.

Methods of oxidation are needed which minimize the production of phenol during oxidation and which preferably also minimize the production of one or more byproducts selected from the group consisting of acetophenone (AP), dimethylbenzyl alcohol (DMBA), and ethyl methyl benzyl carbinol (EMBA).

SUMMARY

The application provides a process for oxidation of alkylbenzenes to produce hydroperoxides. The process comprises providing an oxidation feed consisting essentially of an organic phase. The oxidation feed comprises one or more alkylbenzenes and a quantity of neutralizing base having a pH of from about 8 to about 12.5 in 1 to 10 wt. % aqueous solution. The quantity of neutralizing base is effective to neutralize at least a portion of acids formed during the oxidation. The oxidation feed comprises up to an amount of water effective to increase neutralization of acids formed during the oxidation without forming a separate aqueous phase. The oxidation feed is exposed to oxidation conditions effective to produce an oxidation product stream comprising one or more product hydroperoxides.

DESCRIPTION

The present application relates to a process for producing phenol in which oxidation occurs in the presence of a neutralizing base. The neutralizing base maximizes the production of hydroperoxides while minimizing the production of undesirable by-products.

Portions of the following description are specific to preferred embodiments, in which either s-butylbenzene, alone, or a combination of cumene and s-butylbenzene is fed to the oxidation zone. The neutralizing base is useful during oxidation of other alkylbenzenes, either alone or in combination.

Typically, formic acid and acetic acid, along with AP, EMBA, and DMBA, are produced as by-products from the oxidation of alkylbenzene(s). Formic and acetic acids catalyze the formation of phenol, which is a poison (or inhibitor) of the main oxidation pathway to make the desired products. Formic and acetic acids, and hence phenol, cause a reduction in the formation of desired products relative to by-products.

The yield of hydroperoxides is increased and attendant by-product formation (e.g., AP, DMBA, EMBA) is decreased by the addition of an amount of neutralizing base to the oxidation mixture. Adding a neutralizing base to the oxidation mixture also neutralizes acids, such as acetic acid and formic acid, as they are formed. In this way, the acids are prevented from promoting phenol formation, and the yield of desired hydroperoxide product is maximized.

The quantity of neutralizing base added to the oxidation mixture is sufficient under the oxidation conditions to neutralize at least a portion of acids formed. Preferably, the quantity of neutralizing base is also insufficient to cause the neutralizing base to precipitate out of solution and/or to increase production of one or more materials selected from the group consisting of phenol and one or more byproducts selected from the group consisting of AP, DMBA and EMBA.

Preferably a portion of a solution of the neutralizing base is added separately to each oxidation reactor, most preferably to a series of continuous oxidation reactors. Suitable neutralizing bases are those that have a pH of from about 8 to about 12.5 in 1 to 10 wt. % aqueous solution and include, but are not necessarily limited to alkali bases, anhydrous ammonia, and aqueous ammonia. Compared to an oxidation control experiment performed under the same conditions absent the neutralizing base, preferred neutralizing bases also are effective to perform a function selected from the group consisting of increasing total hydroperoxide yield, decreasing AP formation, decreasing DMBA formation, decreasing EMBA formation, and decreasing phenol formation. Preferably, the neutralizing base achieves one or more of the following compared to the control: increases total hydroperoxide yield by about 7% or more; decreases AP formation by about 20% or more; decreases EMBA and/or DMBA formation by about 20% or more; and, decreases phenol content by about 50% or more.

Preferred alkali bases are alkali metal bases including, but not necessarily limited to alkali metal carbonates and alkali metal bicarbonates. Suitable alkali metals include, but are not necessarily limited to potassium and sodium. A preferred embodiment and a preferred alkali metal base is sodium carbonate. Where an alkali base is used as the neutralizing base, the amount of alkali base preferably is sufficient under the oxidation conditions to neutralize at least a portion of acids formed but insufficient to cause the alkali base to precipitate out of solution in the oxidation mixture. Preferably, the amount of alkali base is an amount sufficient to produce a ratio of alkali base to acids of from about 0.5:1 to about 4:1.

Ammonia is another preferred neutralizing base. The ammonia can be added as gaseous anhydrous ammonia, gaseous anhydrous ammonia along with a small water feed, or aqueous ammonia. Where ammonia is used as the neutralizing base, the amount of ammonia preferably is insufficient to increase production of one or more materials selected from the group consisting of phenol and one or more byproducts selected from the group consisting of AP, DMBA, and EMBA. Preferably, the amount of ammonia is sufficient to produce a molar ratio of ammonia to acids of from about 0.5:1 to about 6:1. A preferred embodiment uses aqueous ammonia.

The total amount of water in the oxidation mixture is an amount effective to increase neutralization of acids formed during oxidation by the neutralizing base without forming a separate aqueous phase. The amount of water in the oxidation mixture preferably is from about 400 ppm to about 2 wt. %. Without limiting the application to a particular mechanism of action, including a small amount of water in the oxidation mixture is believed to improve the solubility of the base in the oxidation mixture, making the base more readily available to perform the neutralization.

The oxidation process comprises an oxidation zone comprising one or more oxidation reactor(s). The oxidation reactor(s) may be batch reactor(s) or continuous reactor(s). In a preferred embodiment, the oxidation zone comprises a series of continuous reactors. An oxidation feed comprising one or more alkylbenzenes is fed to the oxidation reactor(s). The oxidation feed preferably comprises a) cumene; (b) s-butylbenzene, or (c) a combination comprising cumene and s-butylbenzene. In the oxidation reactor(s), the oxidation feed is oxidized by molecular oxygen, preferably air, to produce an oxidation product stream.

The oxidation product stream comprises alkylbenzene hydroperoxide(s) corresponding to the alkylbenzene(s) in the oxidation feed. Where the oxidation feed is cumene, the oxidation product stream comprises cumene hydroperoxide. Where the oxidation feed is s-butylbenzene, the oxidation product stream comprises s-butylbenzene hydroperoxide, but typically does not comprise a significant amount of cumene hydroperoxide. The operating conditions can be adjusted to coproduce more or less acetophenone (AP) and/or other by-products. Where the oxidation feed comprises both cumene and s-butylbenzene, the oxidation product stream comprises s-butylbenzene hydroperoxide and cumene hydroperoxide at high selectivity.

In a preferred embodiment, the oxidation feed comprises a weight ratio of cumene:s-butylbenzene of from about 1:8 to about 2:1. In percentage terms, the foregoing ratios represent from about 12.5 wt. % cumene to about 66.7 wt. % cumene. In another embodiment, the amount of cumene is from greater than 15 wt. % to less than 30 wt. % relative to the content of s-butylbenzene.

Without limiting the claims to a particular mechanism of action unless expressly stated in a claim, the predominate mechanism for the formation of the major and minor by-products (described previously) is believed to be the free radical decomposition of the s-butylbenzene hydroperoxide and (if present) the cumene hydroperoxide in the oxidation product.

In the oxidation reactor(s), the oxidation mixture is contacted with an oxygen-containing gas under oxidation conditions comprising an oxidation temperature effective to oxidize the alkylbenzene(s) to produce the respective hydroperoxides. Suitable oxidation temperatures at most oxidation pressures are from about 90° C. to about 150° C. Preferred temperatures will vary depending upon the type of oxidation reactor and the composition of the oxidation feed. Where the oxidation feed comprises cumene and s-butylbenzene, conversion and selectivity to cumene hydroperoxide and s-butylbenzene hydroperoxide increases with an increase in the cumene:s-butylbenzene ratio in the oxidation feed. Conversion also increases with an increase in oxidation temperature.

In a batch oxidation reactor, the oxidation temperature can be adjusted throughout the reaction period to maximize selectivity of the oxidation reaction. Suitable oxidation pressures for batch reactor(s) are from about 0 psig to about 100 psig, preferably from about 15 psig to about 40 psig.

In continuous oxidation reactor(s), the oxidation temperature in each oxidation reactor is selected to maximize selectivity, and will depend upon the composition of the oxidation feed. Suitable oxidation pressures when using continuous reactors generally are from about 0 psig to about 100 psig, preferably from about 15 psig to about 40 psig. Where the oxidation feed comprises a weight ratio of cumene:s-butylbenzene of 2:1, a preferred oxidation temperature for a continuous reactor is from about 100° C. to about 115° C. Where the oxidation feed comprises a weight ratio of cumene:s-butylbenzene of 1:8, a preferred oxidation temperature for a continuous reactor is from about 110° C. to about 130° C.

Oxidation reaction times will vary from about 5 to about 25 hours. The oxidation reaction time in a batch reactor preferably is from about 6 to about 11 hours for all alkylbenzene ratios, with the oxidation temperature adjusted to maximize selectivity. Where the oxidation reactor(s) are continuous oxidation reactors, the "reaction time" typically is referred to as the total residence time. The total residence time is divided between all of the continuous reactors used. For example, if 5 continuous oxidation reactors are operated in series, the residence time for each oxidation reactor is from about 1 to about 5 hours, with oxidation reaction temperatures for each continuous reactor chosen appropriately to achieve desired conversions. The total residence time can be distributed uniformly or non-uniformly between the oxidation reactors.

Both batch reactors and continuous oxidation reactors produce a total conversion of at least about 5% to the desired hydroperoxide(s). Preferably, total conversion is from about 10% to about 30%, more preferably from about 15% to about 25%.

When carrying out the reaction in multiple continuous reactors, any number of continuous reactors can be employed. Product selectivity is increased by increasing the number of continuous reactors. For example, using two continuous reactors produces a higher yield of the desired hydroperoxide(s) than using only one continuous reactor. In a preferred embodiment, from about 3 to about 8 continuous reactors are used in series. The preferred number of reactors will vary with the alkylbenzenes in the feed. For example, where cumene is fed alone, a preferred number of reactors is four. Where cumene and s-butylbenzene are fed in combination, the preferred number of reactors will vary with the cumene:s-butylbenzene ratio of the oxidation feed. For example, where the oxidation feed comprises a ratio of 2:1 cumene:s-butylbenzene, it is preferred to use 4 reactors. In contrast, where the oxidation feed comprises a ratio of 1:8 cumene:s-butylbenzene, it is preferred to use 5 or 6 reactors.

Where the oxidation reactor is one or more continuous reactor(s), the continuous reactor(s) can be a variety of types, including but not necessarily limited to stirred tank reactor(s) or bubble column reactor(s).

The application will be better understood with reference to the following examples:

EXAMPLE 1

A standard stock oxidation mixture was prepared containing an amount of sec-butyl benzene (sBB), and an amount of cumene effective to produce a weight ratio of sBB:cumene of 3.4:1. The stock oxidation mixture also contained 1% cumene hydroperoxide as an initiator. In all experiments described below, 300 grams of the oxidation mixture was exposed to oxidation conditions comprising a temperature of 130° C., an oxidizing agent comprising 500 cc/min. 7% $O_2$ in $N_2$, and a steady pressure of 40 psig. All experiments were carried out in a 500 cc Buchi Type II reactor, with a stirring rate of 1300 rpm.

The foregoing stock oxidation mixture was used in a control oxidation to provide a comparative example to assess the effect of ammonia on the reaction. Neither ammonia nor water was added to the control experiment. After 8 hours, the mixture contained 340 wppm formic acid, 752 wppm acetic acid, and 515 wppm phenol.

In a first comparative experiment, during the oxidation, gaseous $NH_3$ was bubbled through the oxidation mixture at a molar ratio of 1.28 to 1 based on the expected acid production, resulting in an ammonia feed rate of 0.379 cc/min at STP. No water was added in this experiment.

In a second comparative experiment, 1.25 wt. % water was charged to the standard oxidation mixture, and during the oxidation, gaseous ammonia was bubbled through the oxidation mixture at a molar ratio of $NH_3$ to expected acid production of 1.28 to 1, resulting in a feed rate of the aqueous ammonia of 0.375 cc/min. at STP.

Measurements of cumene hydroperoxide (CHP), s-butyl-benzene hydroperoxide (sBBHP), AP, DMBA, and EMBA were taken every hour, after the reaction temperature reached designed temperature and $NH_3$ feed started. All results listed below are in % wt:

TABLE 1a

Oxidation without NH3

| | Time (hour) | | | | | | | |
|---|---|---|---|---|---|---|---|---|
| | 1 | 2 | 3 | 4 | 5 | 6 | 7 | 8 |
| CHP | 1.9 | 3.1 | 4.1 | 5.2 | 6.5 | 7.4 | 8.2 | 8.7 |
| Sbbhp | 1.5 | 3.8 | 5.9 | 8.2 | 11.0 | 13.3 | 15.2 | 16.8 |
| AP | 0.1 | 0.2 | 0.4 | 0.6 | 1.1 | 1.6 | 2.3 | 3.2 |
| DMBA | 0.2 | 0.3 | 0.4 | 0.5 | 0.8 | 1.1 | 1.6 | 2.1 |
| EMBA | 0.0 | 0.1 | 0.1 | 0.2 | 0.3 | 0.5 | 0.8 | 1.1 |

TABLE 1b

Oxidation with no H2O and NH3 at 1.28:1 NH3 to expected acid amount

| | Time (hour) | | | | | | | |
|---|---|---|---|---|---|---|---|---|
| | 1 | 2 | 3 | 4 | 5 | 6 | 7 | 8 |
| CHP | 1.7 | 2.7 | 3.8 | 5.1 | 6.2 | 7.4 | 8.2 | 8.9 |
| sBBHP | 1.1 | 3.1 | 5.3 | 7.9 | 10.4 | 13.2 | 15.0 | 17.2 |
| AP | 0.1 | 0.2 | 0.4 | 0.6 | 1.0 | 1.6 | 2.2 | 2.9 |
| DMBA | 0.2 | 0.2 | 0.3 | 0.5 | 0.7 | 1.0 | 1.3 | 1.8 |
| EMBA | 0.0 | 0.0 | 0.1 | 0.1 | 0.3 | 0.4 | 0.6 | 0.9 |

TABLE 1c

Oxidation with 1.25% wt H2O and NH3 at 1.28:1 NH3 to expected acid amount

| | Time (hour) | | | | | | | |
|---|---|---|---|---|---|---|---|---|
| | 1 | 2 | 3 | 4 | 5 | 6 | 7 | 8 |
| CHP | 2.0 | 3.3 | 4.4 | 5.5 | 6.7 | 7.7 | 8.8 | 9.4 |
| sBBHP | 1.8 | 4.4 | 6.4 | 8.8 | 11.4 | 13.8 | 16.5 | 18.2 |
| AP | 0.1 | 0.2 | 0.4 | 0.7 | 1.0 | 1.5 | 2.2 | 2.8 |
| DMBA | 0.2 | 0.3 | 0.4 | 0.5 | 0.8 | 1.1 | 1.5 | 1.8 |
| EMBA | 0.0 | 0.1 | 0.1 | 0.2 | 0.3 | 0.4 | 0.7 | 0.9 |

The improvements are summarized in the following Table:

| Summary of improvement as a result of $NH_3$ addition: | | | |
|---|---|---|---|
| | Hydroperoxide yield* | AP** | (DMBA + EMBA)** |
| $NH_3$:acid = 1.28:1 mole:mole, no water | 2.4% | −8.4% | −19.9% |
| $NH_3$:acid = 1.28:1 mole:mole, w/1.25% water | 8.5% | −26.5% | −29.5% |

*Measured at the end of 8 hour
**Measured at 25% wt total hydroperoxide level

After 8 hours, the hydroperoxide yield in the oxidation mixture charged with ammonia but no water was 2.4% higher than in the control, while the hydroperoxide yield in the oxidation mixture charged with both ammonia and water was 8.5% higher than in the control. Interpolating the oxidation results to 25 wt. % total hydroperoxides, the ammonia-charged oxidation mixture exhibited an AP production 26.5% lower than in the control and a DMBA and EMBA production 29.5% lower than in the control.

EXAMPLE 2

A standard oxidation mixture was prepared containing an amount of sec-butyl benzene (sBB) and an amount of cumene effective to produce a weight ratio of sBB:cumene of 3.4:1. The stock oxidation mixture also contained 1% cumene hydroperoxide as an initiator. In all experiments described below, 300 grams of the oxidation mixture was exposed to oxidation conditions comprising a temperature of 130° C., an oxidizing agent comprising 500 cc/min. 7% $O_2$ in $N_2$, and a steady pressure of 40 psig. All experiments were carried out in a 500 cc Buchi Type II reactor, with stirring rate of 1300 rpm.

The foregoing stock oxidation mixture was used in a control oxidation to provide a comparative example to assess the effect of ammonia on the reaction. Neither ammonia nor water was added to the control experiment. After 8 hours, the mixture contained 340 wppm formic acid, 752 wppm acetic acid, and 515 wppm phenol.

In subsequent experiments, 3.8 g of water was added into 300 g of the standard oxidation mixture mentioned in the above paragraph. Gaseous $NH_3$ was bubbled through the sample at various rates, resulting in molar ratios of ammonia to expected acids of 0.0:1, 0.51:1, 1.28:1, 6.8:1 and 15.4:1. Interpolating the oxidation results to 23 wt. % hydroperoxides, the ammonia-charged oxidation mixture exhibited the following results:

| | $NH_3$:acid (mole:mole) | | | | |
|---|---|---|---|---|---|
| | 0 | 0.5:1 | 1.28:1 | 6.8:1 | 15.4:1 |
| Yield changes (@ end of 8 hr run) | −1.6% | 6.5% | 8.5% | −5.4% | −8.3% |
| AP/HP changes | −8.7% | −20.2% | −20.6% | 4.4% | 20.5% |
| Phenol changes | −55.3% | −59.8% | −71.1% | −61.6% | 151.3% |
| Total (DMBA + | −8.3% | −23.5% | −23.9% | −3.5% | 25.2% |

-continued

| | NH₃:acid (mole:mole) | | | |
|---|---|---|---|---|
| | 0 | 0.5:1 | 1.28:1 | 6.8:1 | 15.4:1 |
| EMBA changes | | | | | |

*All experiments above contain 1.25% water. All results obtained were based on comparison with base case which contains no water or NH₃. Comparison of AP/HP, phenol, DMBA + EMBA were made at 23% total HP level In general, hydroperoxide yield improved (up to 8.5% at the end of 8 hour run) where enough NH3 was added to neutralize the expected amount of acids. For the ammonia additions, a reduction of all by-products, as well as phenol poison was also achieved compared to the control experiment. At NH3:acid=1.28:1, AP formation was reduced by 20.6%, DMBA+EMBA was reduced by 23.9% and phenol poison was reduced by 71.1%. When NH3 was added in excessive amount, however, the magnitude of the reduction in by-products and phenol diminished and even increased over the control oxidation. This was clearly demonstrated at NH3:acid=15.4:1, where the total hydroperoxide yield decreased by 8.3%, AP formation increased by 20.5%, and DMBA+EMBA increased by 25.2%. Phenol poison also increased dramatically.

EXAMPLE 3

The same standard oxidation experiment as mentioned in Example 1 and Example 2 was used as a control oxidation to provide a comparative example to assess the effect of sodium carbonate on the reaction. Neither sodium carbonate nor water was added to the control mixture. After 8 hours, the mixture contained 340 wppm formic acid, 752 wppm acetic acid and 515 wppm phenol.

In a comparative experiment, 0.95 g of water along with 0.3 grams of Na2CO3 was added into 300 grams of standard oxidation feed. This resulted in a molar ratio of Na2CO3 to expected acids of 0.9:1 in the oxidation mixture. Compared to the control experiment, total hydroperoxide yield at the end of the 8 hour run increased by 17.1%. Interpolating the experimental results to 25 wt. % total hydroperoxides, the Na2CO3 charged oxidation mixture achieved an AP reduction of 28.7% and a DMBA+EMBA reduction of 33%.

Persons of ordinary skill in the art will recognize that many modifications may be made to the foregoing without departing from the spirit and scope thereof. The embodiment described herein is meant to be illustrative only and should not be taken as limiting the invention, which is defined in the following claims.

We claim:

1. A process for oxidation of alkylbenzenes to produce one or more product hydroperoxides comprising exposing an oxidation feed to oxidation conditions, the oxidation feed consisting essentially of an organic phase, the organic phase comprising one or more alkylbenzenes, an amount of water which is insufficient to form a separate aqueous phase, and a quantity of alkali metal base which is insufficient to precipitate out of solution during oxidation but effective under the oxidation conditions to produce an oxidation product stream comprising a total yield of one or more product hydroperoxides which is greater than that produced in the absence of the alkali metal base.

2. The process of claim 1 further comprising producing said total yield of one or more hydroperoxides which is 7% or more greater than that produced in the absence of the alkali metal base.

3. The process of claim 1 wherein the oxidation feed further consists essentially of from about 400 ppm to about 2 wt. % water.

4. The process of claim 1 wherein the oxidation feed further consists essentially of from about 400 ppm to about 2 wt. % water.

5. The process of claim 1 wherein the alkylbenzenes are selected from the group consisting of cumene, s-butylbenze, and combinations thereof.

6. The process of claim 4 wherein said alkylbenzenes are selected from the group consisting of cumene, s-butylbenzene, and combinations thereof.

7. The process of claim 1 wherein the quantity of alkali metal base is sufficient to produce a molar ratio of from about 0.5:1 to about 4:1 to acids formed during said oxidation.

8. The process of claim 6 wherein said quantity of alkali metal base is sufficient to produce a molar ratio of from about 0.5:1 to about 4:1 to acids formed during said oxidation.

9. The process of claim 1 wherein said alkali metal is selected from the group consisting of sodium and potassium.

10. The process of claim 8 wherein said alkali metal is selected from the group consisting of sodium and potassium.

11. The process of claim 1 wherein said alkali metal base is selected from the group consisting of alkali metal carbonates and alkali metal bicarbonates.

12. The process of claim 10 wherein said alkali metal base is selected from the group consisting of alkali metal carbonates and alkali metal bicarbonates.

13. The process of claim 1 wherein the quantity of alkali metal base is effective to perform a function selected from the group consisting of decreasing acetophenone formation, decreasing dimethyl benzyl alcohol formation, decreasing ethyl methyl benzyl alcohol formation, decreasing phenol content, and combinations thereof.

14. The process of claim 12 wherein the quantity of alkali metal base is effective to perform a function selected from the group consisting of decreasing acetophenone formation, decreasing dimethyl benzyl alcohol formation, decreasing ethyl methyl benzyl alcohol formation, decreasing phenol content, and combinations thereof.

15. The process of claim 2 wherein acetophenone formation is decreased by about 20% or more.

16. The process of claim 12 wherein acetophenone formation is decreased by about 20% or more.

17. The process of claim 2 wherein formation of one or more of dimethyl benzyl alcohol and ethyl methyl benzyl alcohol is decreased by about 20% or more.

18. The process of claim 16 wherein formation of one or more of dimethyl benzyl alcohol and ethyl methyl benzyl alcohol is decreased by about 20% or more.

19. The process of claim 2 wherein phenol content is decreased by about 50% or more.

20. The process of claim 18 wherein phenol content is decreased by about 50% or more.

21. A process for oxidation of alkylbenzenes to produce one or more product hydroperoxides comprising exposing an oxidation feed to oxidation conditions, the oxidation feed consisting essentially of an organic phase, the oxidation feed comprising one or more alkylbenzenes, an amount of water which is insufficient to form a separate aqueous phase, and a quantity of sodium carbonate which is insufficient to precipitate out of solution during oxidation but effective under the oxidation conditions to produce an oxidation product stream comprising a total yield of one or more product hydroperoxides which is greater than that produced in the absence of the sodium carbonate.

22. The process of claim 21 further comprising producing said total yield of one or more hydroperoxides which is 7% or more greater than that produced in the absence of the sodium carbonate.

23. The process of claim 21 wherein amount of water is from about 400 ppm to about 2 wt. % water.

24. The process of claim 22 wherein amount of water is from about 400 ppm to about 2 wt. % water.

25. The process of claim 21 wherein said alkylbenzenes are selected from the group consisting of cumene, s-butylbenzene, and combinations thereof.

26. The process of claim 23 wherein said alkylbenzenes are selected from the group consisting of cumene, s-butylbenzene, and combinations thereof.

27. The process of claim 21 wherein said quantity of sodium carbonate is sufficient to produce a molar ratio of from about 0.5:1 to about 4:1 to acids formed during said oxidation.

28. The process of claim 26 wherein said quantity of sodium carbonate is sufficient to produce a molar ratio of from about 0.5:1 to about 4:1 to acids formed during said oxidation.

29. The process of claim 21 wherein the quantity of sodium carbonate is effective to perform a function selected from the group consisting of decreasing acetophenone formation, decreasing dimethyl benzyl alcohol formation, decreasing ethyl methyl benzyl alcohol formation, decreasing phenol content, an combinations thereof.

30. The process of claim 28 wherein the quantity of sodium carbonate is effective to perform a function selected from the group consisting of decreasing acetophenone formation, decreasing dimethyl benzyl alcohol formation, decreasing ethyl methyl benzyl alcohol formation, decreasing phenol content, and combinations thereof.

31. The process of claim 21 wherein acetophenone formation is decreased by about 20% or more.

32. The process of claim 28 wherein acetophenone formation is decreased by about 20% or more.

33. The process of claim 21 wherein formation of one or more of dimethyl benzyl alcohol and ethyl methyl benzyl alcohol is decreased by about 20% or more.

34. The process of claim 32 wherein formation of one or more of dimethyl benzyl alcohol and ethyl methyl benzyl alcohol is decreased by about 20% or more.

35. The process of claim 21 wherein phenol content is decreased by about 50% or more.

36. The process of claim 34 wherein phenol content is decreased by about 50% or more.

* * * * *